(12) United States Patent
Brown et al.

(10) Patent No.: US 12,134,762 B2
(45) Date of Patent: Nov. 5, 2024

(54) LYMPHOVASCULAR INVASION BIOREACTOR AND METHODS OF MAKING AND USING SAME

(71) Applicant: Duke University, Durham, NC (US)

(72) Inventors: David Brown, Durham, NC (US); Gayathri Devi, Durham, NC (US)

(73) Assignee: Duke University, Durham, NC (US)

( * ) Notice: Subject to any disclaimer, the term of this patent is extended or adjusted under 35 U.S.C. 154(b) by 977 days.

(21) Appl. No.: 16/762,857

(22) PCT Filed: Nov. 9, 2018

(86) PCT No.: PCT/US2018/060016
§ 371 (c)(1),
(2) Date: May 8, 2020

(87) PCT Pub. No.: WO2019/094710
PCT Pub. Date: May 16, 2019

(65) Prior Publication Data
US 2021/0171893 A1 Jun. 10, 2021

Related U.S. Application Data

(60) Provisional application No. 62/583,662, filed on Nov. 9, 2017.

(51) Int. Cl.
| C12M 1/42 | (2006.01) |
| C12M 1/00 | (2006.01) |
| C12M 1/12 | (2006.01) |
| G01N 33/50 | (2006.01) |
| G01N 33/574 | (2006.01) |

(52) U.S. Cl.
CPC ............ *C12M 35/08* (2013.01); *C12M 23/14* (2013.01); *C12M 25/04* (2013.01); *G01N 33/5017* (2013.01); *G01N 33/57415* (2013.01)

(58) Field of Classification Search
CPC ...... C12M 35/08; C12M 23/14; C12M 25/04; G01N 33/5017; G01N 33/57415
USPC ..................................................... 435/287.2
See application file for complete search history.

(56) References Cited

U.S. PATENT DOCUMENTS

| 2013/0189723 A1* | 7/2013 | Felder .................... C12M 25/16 435/287.7 |
| 2013/0280807 A1* | 10/2013 | Takezawa .............. C12M 21/08 156/230 |
| 2016/0340635 A1* | 11/2016 | Kirshner ................ C12M 25/14 |
| 2017/0020828 A1 | 1/2017 | Devi |

FOREIGN PATENT DOCUMENTS

| WO | 2014126228 A1 | 8/2014 |
| WO | 2015094123 A1 | 6/2015 |
| WO | WO-2016004015 A1 * | 1/2016 ............ C12M 21/08 |

OTHER PUBLICATIONS

Corning Transwell Wayback Date Page (Year: 2015).*
Corning Transwell Permeable Supports p. 2 (Year: 2015).*
(Continued)

*Primary Examiner* — Michael L Hobbs
(74) *Attorney, Agent, or Firm* — Quarles & Brady, LLP

(57) ABSTRACT

The present disclosure comprises a lymphovascular bioreactor system and methods of making and using same.

17 Claims, 4 Drawing Sheets

(56) References Cited

OTHER PUBLICATIONS

Disulfiram (DSF) acts as a copper ionophore to induce copper-dependent oxidative stress and mediate anti-tumor efficacy in inflammatory breast cancer (Year: 2015).*

Arora, J., et al. "Inflammatory breast cancer tumor emboli express high levels of anti-apoptotic proteins: use of a quantitative high content and high-throughput 3D IBC spheroid assay to identify targeting strategies." Oncotarget 8.16 (2017): 25848.

International Searching Authority. International Search Report and Written Opinion for application PCT/US2018/060016. Mailed on Feb. 25, 2019. 14 pages.

Lehman, H. L., et al. "Modeling and characterization of inflammatory breast cancer emboli grown in vitro." International journal of cancer 132.10 (2013): 2283-2294.

Mu, Z., et al. "EZH2 knockdown suppresses the growth and invasion of human inflammatory breast cancer cells." Journal of experimental & clinical cancer research 32.1 (2013): 1-9.

Price, A., et al. "Elucidating a role for the translation initiation factor, eIF4G1, in resistance to therapy in inflammatory breast cancer (IBC)." (2015): 1007-1007.

* cited by examiner

LYMPHOVASCULAR INVASION BIOREACTOR AND METHODS OF MAKING AND USING SAME

CROSS-REFERENCES TO RELATED APPLICATIONS

This patent application is a national stage filing under 35 U.S.C. 371 of International Application No. PCT/US2018/060016, filed Nov. 9, 2018, which claims the benefit of priority to U.S. Provisional Patent Application No. 62/583,662, filed Nov. 9, 2017, both of which are incorporated herein by reference in their entirety.

STATEMENT REGARDING FEDERALLY SPONSORED RESEARCH

This invention was made with Government support under FY16 Breakthrough Award Funding Level 2 awarded by the Department of Defense. The Federal Government has certain rights to this invention.

BACKGROUND OF THE INVENTION

Inflammatory breast cancer (IBC) is the deadliest, distinct subtype of breast cancer. A hallmark of IBC is its propensity for dermal lymphovascular invasion (LVI), which is characterized by dilated dermal lymphatic spaces filled with tumor emboli that generally remain detached from the surrounding vascular endothelium. Regional lymph node involvement and distant metastasis is common, although the mechanisms of tumor cell exfiltration from the lymphatic system are poorly understood.

A growing body of evidence indicates that LVI is related to the ability of IBC to escape immune surveillance and killing. Our group previously demonstrated that LVI is related to an immunosuppressive phenotype of IBC. This phenotype is characterized by variations in 79 genes largely related to immunosuppressive functions as well as anti-apoptotic, antioxidant, and proliferative pathways governed by the nuclear transcription factor NFκB. Although a number of genes can modulate NFκB, we have identified a critical role of the X-linked inhibitor of apoptosis protein (XIAP). XIAP is a member of the inhibitor of apoptosis protein (IAP) family and is involved in the direct activation of NFκB and its target genes. Importantly, there appears to exist a link between XIAP expression and tumor invasiveness: XIAP expression correlates with increased tumor stage and grade in patients with IBC, while knockdown of XIAP completely abrogates tumor growth in mice. Despite the importance of XIAP in cancer progression, its mechanistic role in LVI is not well understood. This is largely due to the limited capacity of existing in vitro models to simulate LVI. 2D co-culture and cell migration assays do not adequately depict spatially-relevant cell-cell and cell-matrix interactions that exist in vivo, particularly in dynamic systems such as the tumor-lymphovascular interface.

SUMMARY OF THE INVENTION

This disclosure provides, in part, a novel lymphovascular bioreactor system designed to model lymphovascular invasion for tumors. In some embodiments, cells are harvested from a patient and combined in the bioreactor to model the process of lymphovascular metastasis. The present invention also provides in some embodiments methods of testing anticancer drugs in the bioreactor system, and in some aspects, patient-specific screening and data on efficacy of different therapies. Other embodiments of the present disclosure provide methods for determining drug efficacy against a tumor, methods of designing a patient-specific anticancer therapy, and methods of determining the efficacy/prognosis of an anticancer therapy in a subject using the bioreactors provided herein.

In one aspect, the disclosure provides an in vitro 3-D lymphovascular system comprising: (a) a fluid chamber comprising medium in liquid communication with a transwell and a fluid pump, (b) the transwell comprising a permeable membrane separating a basolateral surface and an apical compartment of the transwell, wherein the apical surface of the transwell comprises: (i) lymphatic endothelial cells (LECs) seeded on the apical surface of the permeable membrane; (ii) a layer of hydrogel above the seeded LECs layer, and (iii) medium comprising tumor cells; and (c) a fluid pump capable of creating steady-state flow rate of medium throughout the fluid chamber and transwell of the system.

In another aspect, the present disclosure provides a method of testing the efficacy of an anti-cancer therapy, the method comprising contacting the 3-D lymphovascular system described herein with the anti-cancer therapy; and measuring the efficacy of the therapy.

In another aspect, the present disclosure provides a method of screening for a patient-specific anticancer therapy, the method comprising: contacting a plurality of 3-D lymphovascular systems described herein each with a different anticancer therapy, and assessing the efficacy of each anticancer therapy against the patient specific tumor cells in the system.

In yet another aspect, the present disclosure provides a kit for producing a patient-specific 3-D lymphovascular system, the kit comprising: (a) a fluid chamber, (b) a transwell, (c) a fluid pump, (d) culture medium, and instructions for producing the patient-specific 3-D lymphovascular system.

These and other features, aspects, and advantages of the present invention will become better understood upon consideration of the following detailed description, drawings and appended claims.

DETAILED DESCRIPTION OF THE INVENTION

Figure 1A:
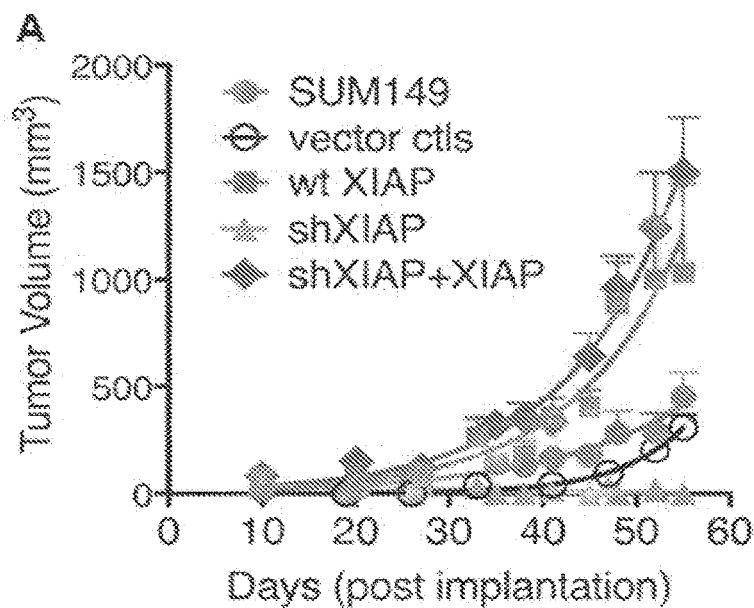
FIGS. 1A-1C are images demonstrating XIAP effects tumor growth. A. Accelerated tumor growth rate in wtXIAP bearing mice compared to control SUM149. Strikingly, shXIAP tumors grew to palpability and either completely regressed or did not increase in size in the study period. XIAP reexpression in shXIAP cells (+XIAP) increased tumor growth revealing the necessity for XIAP expression. Representative image of wtXIAP with extensive secondary clusters of tumor cells in local and distant sites (lung tissue luciferase imaging) B. XIAP staining identified in primary IBC tumors and emboli compared to negative staining in benign breast tissue. C. Application of the IBC patient-derived 79 gene signature to the XIAP modulated cells show that as expected patient-derived SUM149 are highly IBC-like with an average posterior probability (similarity) of 44.7% and the XIAP overexpressing (wtXIAP) cells with posterior IBC probability (i.e. 51.5%). However, knock down of XIAP (shXIAP) completely abolishes any resemblance to the 79-gene IBC patient gene signature (i.e. 0.05%). (parts from Arora, Oncotarget in press, Abstract; Price, 2015 Abstract).

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates. It is also to be understood that the terminology used herein is for the purpose of describing particular embodiments only, and is not intended to be limiting. The scope of the present invention will be limited only by the claims.

Articles "a" and "an" are used herein to refer to one or to more than one (i.e. at least one) of the grammatical object of the article. By way of example, "an element" means at least one element and can include more than one element.

"About" is used to provide flexibility to a numerical range endpoint by providing that a given value may be "slightly above" or "slightly below" the endpoint without affecting the desired result. About when used in reference to a number, in some instances, provides +/−10% of the numerical value.

The use herein of the terms "including," "comprising," or "having," and variations thereof, is meant to encompass the elements listed thereafter and equivalents thereof as well as additional elements. Embodiments recited as "including," "comprising" or "having" certain elements are also contemplated as "consisting essentially of and" consisting of those certain elements. Variations of the term "comprising" should be interpreted as referring to elements, components, or steps in a non-exclusive manner, so the referenced elements, components, or steps may be combined with other elements, components, or steps that are not expressly referenced.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. In other words, in places where ranges of values are given, this disclosure explicitly contemplates other combinations of the lower and upper limits of those ranges that are not explicitly recited. For example, recitation of a value between 1 and 10 or between 2 and 9 also contemplates a value between 1 and 9 or between 2 and 10. Ranges identified as being "between" two values are inclusive of the end-point values. For example, recitation of a value between 1 and 10 includes the values 1 and 10.

As used herein, "treatment," "therapy" and/or "therapy regimen" refer to the clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition.

The term "effective amount" or "therapeutically effective amount" refers to an amount sufficient to effect beneficial or desirable biological and/or clinical results.

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like.

Unless otherwise defined, all technical terms used herein have the same meaning as commonly understood by one of ordinary skill in the art to which this disclosure belongs.

The present disclosure provides, in part, a novel lymphovascular bioreactor system designed to model lymphovascular invasion for tumors. In some embodiments, cells are harvested from a patient and combined in the bioreactor to model the process of lymphovascular metastasis, which is a key step in the progression of many solid tumors, including breast cancer. Anticancer drugs can be tested in the bioreactor system, which can provide patient-specific data on efficacy of different therapies. Further, key aspects of lymphovascular invasion (e.g., malignant cell migration) can be quantified in the bioreactor, which also can yield data in prognosis for individual patients. Other embodiments of the present disclosure provide methods for determining drug efficacy against a tumor, methods of designing a patient-specific anticancer therapy, and methods of determining the efficacy/prognosis of an anticancer therapy in a subject using the bioreactors provided herein.

The present invention provides an in vitro 3-D lymphovascular system that recreates the 3-D interactions between tumor cells and the lymphatic system. This system comprising (a) a fluid chamber comprising medium in liquid communication with a transwell and a fluid pump, (b) the transwell comprising a permeable membrane separating a basolateral surface and an apical compartment of the transwell, wherein the apical compartment of the transwell comprises (i) lymphatic endothelial cells seeded on the apical surface of the permeable membrane; (ii) a layer of hydrogel above the seeded LECs layer, and (iii) medium comprising tumor cells; and (c) a fluid pump capable of creating steady-state flow rate of medium throughout the fluid chamber and transwell of the system.

Figure 2:
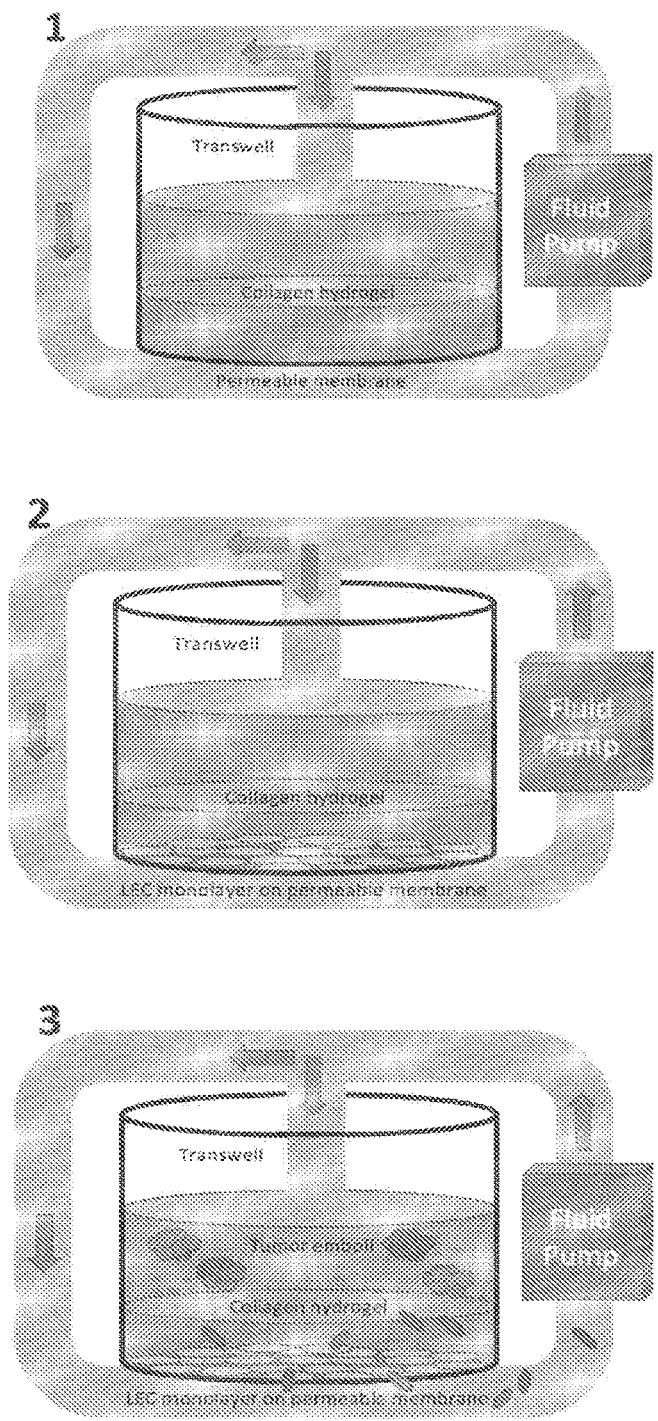
FIG. 2 is a schematic showing staged testing of invasion model as described in the Examples. Experiment 1 involves flow across a cell-free hydrogel to simulate the lymphovascular interstitium, which will be performed for system optimization. Experiment 2 includes an LEC monolayer to simulate the lymphovascular endothelium. Experiment 3 adds IBC tumor emboli to the culture medium overlying the hydrogel to model lymphovascular invasion.
Figure 3:
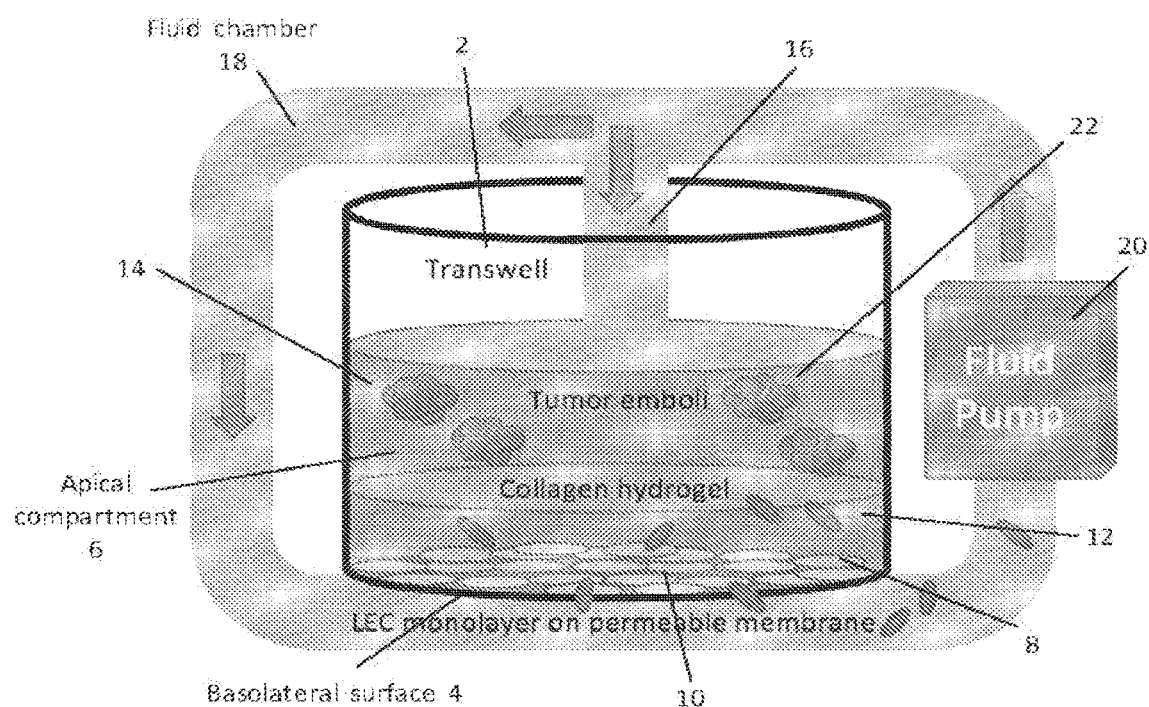
FIG. 3 is a schematic showing a exemplary lymphovascular bioreactor system.

An exemplary lymphovascular bioreactor model is described in FIGS. 2 and 3. As depicted in FIG. 3, a transwell (2) with a basolateral surface (4) in liquid communication with the fluid chamber (18), an apical compartment (6), and a permeable membrane (8) separating the basolateral surface and apical compartment. Lymphatic endothelial cells (LECs, 10) are cultured on the apical side of the permeable membrane. The apical compartment of the transwell further comprises a layer of hydrogel (12) and medium (14) in fluid communication (16) with the fluid source (18).

In some embodiments, the fluid chamber is fabricated with 3D printing and/or stereolithography. Suitable chamber materials are known in the art that are compatable with tissue culture systems including, but not limited to, high-density polyethylene, polystyrene, or polytetrafluoroethylene. These materials can withstand repeated cycles of sterilization with alcohol-based or ethylene chloride-based disinfectants. Connections and tubing are also know in the art and include, but are not limited to, for example, commercially available medical-grade silicone or polyethylene.

Suitable fluid pumps are known in the art. In one embodiment, fluid will be propelled with 3 variable-flow peristaltic pumps, which provides adequate flow without sacrificing cell viability. A pump controller will maintain flow rates such that the system will remain at steady-state. In some embodiments, the flow rate is about 1 mL/min or less.

Suitable cell-permeable membrane are known in the art and include, but are not limited to, for example, tissue culture well plate insert (Transwell, Corning) as the bottom support for the chamber. Suitable pore diameter of the membrane include diameters sufficient to support cell migration, for example, from about 5 μm to about 8.0 μm.

In some embodiments, the system will include a second membrane downstream in the tubing to capture invaded cells. In some embodiments, these invaded cells can be quantified (e.g. via hemacytometer quantitation).

All fluid in the system will be cell culture medium. The chamber will be maintained in a standard tissue conditions, for example, in an incubator at 37° C. with 5% carbon dioxide.

In some embodiments, the LECs are from tissue culture cell lines, for example, but not limited to, primary human dermal LECs (PromoCell) which can be expanded in in culture using Endothelial Cell Growth Medium MV2 (PromoCell) including fetal calf serum. In other embodiments, the LECs may be patient derived, e.g. cells derived from surgery or a biopsy. In suitable embodiments, the LECs are grown into a confluent monolayer before being added to the system. Methods of growing and assessing a confluent monolayer are known in the art. In some embodiments, the LECs form a cell monolayer. A cell monolayer is a layer of densely packed cells that form tight junctions between the cells and allow for transport of interstitial fluid and proteins through the cellular layer.

Suitable tumor cells for use in the present system are tumor cell lines or primary tumor cells obtained from a patient. Suitable tumor cells are breast cancer cells. In some examples, the tumor cells are inflammatory breast cancer (IBC) cells. Suitable tumor cell lines include breast cancer cells, for example, inflammatory breast cancer cells (IBC cells) for example, but not limited to, triple negative SUM-149 and HER-2 overexpressing SUM-190 cell lines (Lehman et al. 2013; Mu et al. 2013). In other examples, the tumor cells are IBC tumor emboli. Tumor emboli are tumor cells that separate from the primary tumor mass and form multicellular spheroids, termed tumor emboli, which then invade through the lymphatic system and reach distant organs to form secondary tumors.

In other embodiments, the suitable tumor cells are tumors obtained from a patient, for example, through surgery or biopsy. Methods of obtaining and culturing primary tumor cells or tumor emboli are known in the art. In some embodiments, the tumor cells are patient specific.

In some embodiments, the tumor cells are obtained from the same patient as the LECs.

In some embodiments, the tumor cells added to the system are tumor emboli. Suitable methods of isolating or culturing tumor emboli are known in the art. For example, IBC tumor emboli may be cultured by culturing IBC cells (either from a patient or a cell line) in a polyethylene glycol (PEG)- or hyaluronic acid-containing medium in ultra-low attachment plates on a shaker plate, which mimics the viscosity and shear forces of lymphatic fluid.

Suitable hydrogels for forming a layer on top of the LEC monolayer are known in the art. The hydrogels will have suitable characteristics to allow for the passage of fluid through the hydrogel to the LECs. The hydrogels also allow for tumor infiltration into the hydrogel in order to mimic in vivo tumor infiltration. Suitable hydrogels are known in the art and include, but are not limited to, for example, collagen hydrogels (e.g., type I collagen hydrogels), synthetic polymer hydrogels, among others. Suitably, the hydrogel is deposited above the LEC monolayer in a thin film of less than 2 mm thickness, preferably less than 1 mm in thickness (e.g., from about 0.1 mm to about 2 mm thick, preferably from about 0.1 mm to about 1 mm thick).

Suitable methods of producing the hydrogel layers are known in the art, for example, type I collagen (Fisher Scientific) can be acidified to make soluble and neutralized with dilute sodium hydroxide at 4° C. The mixture will be deposited on top of the membranes containing confluent LEC monolayers to form a thin (<1 mm) hydrogel film.

In some embodiments, the fluid chamber is in communication with a fluid pump that provides a steady state fluid flow to the system.

The 3-D lymphovascular bioreactor system described herein can be used for methods of testing efficacy or screening of new anti-cancer therapies. In one embodiment, the present invention provides a method of testing the efficacy of an anti-cancer therapy, the method comprising contacting the 3-D lymphovascular system described herein with the anti-cancer therapy and subsequently measuring the efficacy of the therapy.

Suitable methods of determining the efficacy of the therapy are known in the art for in vitro system. For example, the efficacy of the therapy may be assessed by determining the inhibition of tumor cell growth or by determining the percentage of tumor cells killed by the anti-cancer therapy in the system. Methods of assessing tumor cell growth or inhibition or tumor cell death are known in the art. For example, methods of assessing cell death include, but are not limited to, for example, cellular viability testing (trypan blue and hemacytometer analysis, other cell viability staining).

Any suitable anti-cancer therapy may be tested in the system described herein. Suitable anti-cancer drugs are known in the art. In some embodiments, the anti-cancer therapy is a combination of two or more anti-cancer drugs.

In some embodiments, the patient-specific lymphovascular system described herein is used to assess the specific efficacy on an anti-cancer drug for a patient-specific tumor.

In another embodiment, the present invention provides a method of screening for an anticancer therapy, and in some embodiments, a patient-specific anti-cancer therapy. The method comprises: contacting a plurality of 3-D lymphovascular systems described herein each with a different anticancer therapy, and assessing the efficacy of each anti-cancer therapy against the tumor cells in the system. For a patient-specific anti-cancer therapy, the lymphovascular system described herein can be formed using patient derived tumor cells. In some embodiments, the anticancer drug may be a small molecule.

Suitably, the anticancer agent may be able to selectively increase the cell death of tumor cells within a patient, leading to a reduction in the size of tumors, inhibition of tumor growth and/or reduction or inhibition of metastasis.

In another embodiment, the present disclosure provides a method of treating a patient having cancer, the method comprising administering a therapeutically effective amount of an anticancer agent, the anticancer agent being selected from the anticancer agent assessed for efficacy on a patient-specific lymphovascular system as described herein. The methods of screening for effective anticancer therapies can then be used for treating the patient from whom the tumor cells were derived. In a preferred embodiment, the patient has breast cancer, preferably inflammatory breast cancer (IBC).

The "treating" or "treatment" of breast cancer includes, but not limited to, reducing, inhibiting or preventing the growth of cancer cells, reducing, inhibiting or preventing metastasis of breast cancer cells and/or reducing, inhibiting or preventing one or more symptoms of breast cancer or metastasis thereof.

The terms "tumor cell growth" or "tumor cell proliferation" are used herein interchangeably to refer to the increase in number of tumor cells.

The terms "cancer" and "tumor" are used herein interchangeably. The terms "breast cancer" or "breast tumor" refer to or describe the physiological condition in mammals in which a population of cells are characterized by unregulated cell growth that originates in the breast tissue of the mammal. All stages of breast cancer are included, including primary cancer or a secondary (metastatic) lesions thereof. Examples of breast cancer include, but are not limited to, advanced stage breast cancer, inflammatory breast cancer, metastatic reoccurrence, secondary tumors originating from breast cancer, among others.

The term "subject suffering from breast cancer" refers to a subject that presents one or more symptoms indicative of a breast cancer (e.g., a noticeable lump or mass) and/or metastasis thereof, or has been diagnosed as having breast cancer or metastasis thereof.

The term "metastasis" or "secondary tumor" refers to cancer cells that have spread to a secondary site, e.g., outside of the breast tissue. Secondary sites include, but are not limited to, the lymphatic system, skin, distant organs (e.g., liver, stomach, pancreas, brain, etc.) and the like.

In some aspects, the method of treating breast cancer comprises administering the pharmaceutical composition prior to, concurrently with, or after treatment with standard therapies. Suitable standard therapies include, but are not limited to, surgery (e.g. lumpectomy or mastectomy), radiation therapy (RT), and chemotherapy (CT), among others.

In some aspects, the method of treating breast cancer include inhibiting X-linked inhibitor of apoptosis protein (XIAP, also known as inhibitor of apoptosis protein 3 (IAP3)) expression in cancer cells. XIAP is a potent mammalian caspase inhibitor and anti-apoptotic protein.

Aspects of the disclosure described with respect to the former method can be applicable to the latter method, and vice versa, unless the context clearly dictates otherwise.

The methods disclosed herein can include a conventional treatment regimen, which can be altered to include the steps of the methods described herein.

Aspects of the present disclosure that are described with respect to methods can be utilized in the context of the system or kits discussed in this disclosure. Similarly, aspects of the present disclosure that are described with respect to the system can be utilized in the context of the methods and kits, and aspects of the present disclosure that are described with respect to kits can be utilized in the context of the methods and systems.

This disclosure provides kits. The kits can be suitable for use in the methods described herein. Suitable kits include a kit for creating an in vitro 3-D lymphovascular system. In one embodiment, the kit comprises (a) a fluid chamber, (b) a transwell, (c) a fluid pump, (d) culture medium, and instructions for producing the in vitro 3-D lymphovascular system. In some embodiments, the kit provides instructions for making a patient-specific 3-D lymphovascular system using tumor and LECs isolated from a patient.

The following non-limiting examples are included for purposes of illustration only, and are not intended to limit the scope of the range of techniques and protocols in which the compositions and methods of the present invention may find utility, as will be appreciated by one of skill in the art and can be readily implemented.

Example 1: In Vitro Lymphovascular Bioreactor as a Model of 3-D Tumor Emboli and LVI In this Example, we construct a staged, tissue-engineered model of IBC invasion based on 3D tumor emboli, lymphovascular endothelial (LEC) and IBC cell co-culture, and dynamic fluid transport. Initial experiments test A. initial optimization of fluid dynamics, B. flow through an LEC monolayer, and C. IBC tumor emboli invasion.

The resulting lymphovascular bioreactor can be used as a patient-specific, in vitro model of LVI by using patient-specific cells. This bioreactor (3-D cell culture system) can be applied to not only IBC but a wide variety of breast and non-breast cancers. Additionally, we expect to confirm that the immunosuppressive phenotype is associated with a higher rate of LVI in the model. Future studies with this model will focus on the mechanistic role of XIAP in LVI, as well as the development of a clinical assay for LVI.

Inflammatory breast cancer (IBC) is the deadliest, distinct subtype of breast cancer. A hallmark of IBC is its propensity for dermal lymphovascular invasion (LVI), which is characterized by dilated dermal lymphatic spaces filled with tumor emboli that generally remain detached from the surrounding vascular endothelium. Regional lymph node involvement and distant metastases are common, although the mechanisms of tumor cell exfiltration from the lymphatic system are poorly understood1. The presence of dermal and lymphatic invasion (LVI) is reported to be an independent predictor of clinical outcome in terms of shorter breast cancer-specific survival and shorter disease-free metastatic survival. Because of the dominant role of LVI in cancer progression, the underlying mechanisms of LVI must be understood in order to develop novel therapies for IBC.

A growing body of evidence indicates that LVI is related to the ability of IBC to escape immune surveillance and killing. Despite the rich concentration of immune cells within lymphatic vessels, IBC tumor emboli largely avoid immune-mediated destruction. Previous work by our group identified an immunosuppressive phenotype of IBC that renders tumor cells resistant to killing by natural killer (NK) cells and cytotoxic T lymphocytes (CTLs). This phenotype is characterized by variations in 79 genes predominantly related to immunosuppressive functions as well as anti-apoptotic, antioxidant, and proliferative pathways governed by the nuclear transcription factor, NFκB.

Although a number of genes can modulate NFκB, we have identified a critical role of the X-linked inhibitor of apoptosis protein (XIAP). XIAP is a member of the inhibitor of apoptosis protein (IAP) family and is involved in the direct activation of NFκB and its target genes. Importantly, there appears to exist a link between XIAP expression and tumor invasiveness. XIAP expression correlates with increased tumor stage and grade in patients with IBC. In transgenic mice overexpressing XIAP, IBC tumors exhibit enhanced tumor growth as well as an increased rate of metastasis. Conversely, knockdown of XIAP in mice completely incapacitated tumor growth, which was reversed by reconstitution with the XIAP protein. In the XIAP knockdown mice, gene expression analysis revealed a total disappearance of the 79-gene signature, highlighting the critical role of this single gene in the immunosuppressive phenotype. Taken together, these data strongly suggest that XIAP is a key molecular regulator of IBC invasiveness, and therefore represents a very promising therapeutic target.

Despite the importance of XIAP in IBC progression, its mechanistic role in LVI is not well understood. LVI requires production of extracellular matrix (ECM)-degrading enzymes such as MMP-9, which is thought to drive malignant progression of triple negative breast cancer. Our current in vivo model of LVI utilizes a transgenic mouse model bearing a fluorescent reporter on a transgene encoding for the Prox1 regulatory sequence, which allows for RFP expression specifically in lymphatic vessels[10]. While this model provides robust imaging capabilities for lymphatic invasion in vivo, it is limited by the availability and resource-intensiveness of transgenic mice, as well as the inability to study human tissue. A critical need exists to develop an in vitro model of LVI that can be used to study fundamental interactions between IBC cells and the lymphovascular endothelium.

Existing in vitro models of LVI are extremely limited in their ability to model human tumors. LVI is typically studied with simple two-dimensional (2D) cell migration assays such as the transwell assay, cell exclusion zone assay, and fence assay. These techniques can provide useful information on cell-cell interactions, adhesion, and chemotaxis[11]. However, they are ultimately limited by their poor resemblance to native tumors, as they do not adequately depict the spatially-relevant cell-cell and cell-matrix interactions that exist in vivo, particularly in dynamic systems such as the tumor-lymphovascular interface. For some time it has been known that 2D-cultured cells undergo cytoskeletal rearrangements, acquiring artificial polarity, which in turn causes aberrant gene and protein expression in comparison to 3D-cultured cells. The scale-up to 3D model systems allows a closer portrayal of these interactions, as well as more physiologically-relevant gene expression, signaling pathway profiles, heterogeneity, and structural complexity[15].

To this end, we have developed a 3D tumor emboli model that recapitulates many aspects of IBC tumor growth in vivo. Tumor emboli consist of tight cell clusters similar to those observed in IBC with respect to size, composition, and E-cadherin expression[16]. In order to study cell health indicators in tumor emboli, we have recently optimized a novel high-content assay that utilizes combinations of nuclear, viability, and mitochondrial dyes. With this progress in recreating tumor emboli structure, our next objective is to expand the model to simulate the dynamics of LVI.

Tissue engineering (TE) represents a promising approach to designing more sophisticated 3D cell culture models. In its most basic form, TE employs isolated cells that are cultured in 3D extracellular matrix-like "scaffolds" within a controlled microenvironment. Other investigators have attempted to construct TE models of LVI with some success. A 2015 report described invasion of glioblastoma spheroids into a basement membrane matrix, which could be quantified by imaging cytometer. Most relevantly, Pisano et al. described a 3D, multilayered, dynamic flow model comprised of colon cancer cells and primary lymphatic endothelial cells (LECs). In this system, a collagen hydrogel was used to simulate the interstitial tissue, along with low-flow perfusion to simulate interstitial fluid movement and lymph flow. Tumor cell migration was observed through the hydrogel and LEC layer, thus successfully recapitulating the key event in tumor metastasis. An essential feature of this model was the inclusion of an LEC layer to simulate the lymphatic endothelium, as well as the demonstration that cancer cells will invade through this layer. A similar model for IBC has not been described, nor has the use of 3D tumor emboli in a breast cancer invasion model.

The present Example constructs a novel tissue-engineered model based on successful features of both the tumor emboli and dynamic flow models to provide a next-generation model of LVI that will combine 3D cell culture methods, LEC co-culture, and dynamic fluid transport. The model can be used to test breast cancer immunotherapy, including. The theory that XIAP is associated with LVI in vitro.

The model uses triple-negative breast cancer (TNBC) cell lines. Incorporation of both IBC tumor cells and LECs harvested from mastectomy specimens into a tissue-engineered model of LVI can serve as an advanced clinical assay for testing response to chemotherapy and providing prognostic data.

The use of multilayered, 3D tissue models offers significant advantages over 2D culture systems, though these models have not found widespread use in cancer research due to the expertise required to build them. The model described herein does not exist in the breast cancer literature, and could potentially contribute to the wider study of LVI. We will demonstrate a novel clinical assay for measuring TNBC tumor invasiveness and response to chemotherapy: By using tumor cells and LECs isolated from TNBC patients, we test the concept that the tissue-engineered model can be applied as a clinical assay. To our knowledge, no such models exist in breast cancer care where cells are isolated from discarded tissue in surgery and co-cultured in the laboratory. Given the importance of XIAP in immune suppression, a major mechanistic contribution of this study will be in vitro evidence to support the relationship with LVI. This will lead to future studies exploring XIAP as a potential therapeutic target.

An exemplary lymphovascular bioreactor model is described in FIGS. 2 and 3. As depicted in FIG. 3, a transwell (2) with a basolateral surface (4) in liquid communication with the fluid chamber (18), an apical compartment (6), and a permeable membrane (8) separating the two compartments. Lymphatic endothelial cells (LECs, 10) are cultured on the apical side of the permeable membrane. The apical compartment of the transwell further comprises a layer of hydrogel (12) and medium (14) in fluid communication (16) with the fluid source (18). The can be a collagen hydrogel and simulates the lymphovascular interstitium. Type I collagen represents a standard hydrogel platform for 3D culture, and has been shown to promote favorable adhesion and growth of human dermal LECs. It is also derived from benign tissue (rat tail), which provides a noncancerous substrate for invasion. An alternative to hydrogel is a tumor membrane matrix described in Experiment 3 below. The hydrogel bulk provides the medium to observe tumor cell migration by histologic sectioning. Tumor cells (22) are provided in the medium above the collagen hydrogel within the apical compartment.

The dynamic flow system includes a fluid pump to allow for medium movement between the apical compartment and basolateral compartment.

The tumor cells can form tumor emboli in the apical compartment, and the dynamic flow system models tumor cell invasion and transmigration through the hydrogel-LEC complex. Similar to in vivo lymphatic dissemination, interstitial fluid transport may direct tumor cell migration from the tumor towards the lymphatics, thus passively increasing the concentration of malignant cells that reach the lymphatic space. Analysis will be performed to measure cellular viability and qualitative cell morphology within the hydrogel.

Methods: Model fabrication: A prototype fluid chamber will be designed with computer-aided design software (AutoCAD) and fabricated with 3D printing and stereolithography at the Duke Innovation Co-Lab. The chamber material will be high-density polyethylene, polystyrene, or polytetrafluoroethylene which can all withstand repeated cycles of sterilization with alcohol-based or ethylene chloride-based disinfectants. Connections and tubing will be commercially available medical-grade silicone or polyethylene. Fluid will be propelled with 3 variable-flow peristaltic pumps, which provide adequate flow without sacrificing cell viability. A pump controller will maintain flow rates such that the system will remain at steady-state. A cell-permeable membrane or tissue culture well plate insert (Transwell, Corning) will be used as the bottom support for the chamber. Pore diameter of the membrane for initial testing will be 5.0-8.0 µm, which is a diameter sufficient to support cell migration. A second membrane will be used downstream in the tubing to capture invaded cells, which will allow hemacytometer quantitation. All fluid in the system will be cell culture medium. The chamber will be maintained in a standard tissue incubator at 37° C. with 5% carbon dioxide. Cell culture: Primary human dermal LECs (PromoCell) will be expanded in culture using Endothelial Cell Growth Medium MV2 (PromoCell) including fetal calf serum. IBC cells will consist of SUM-149 and SUM-190 cell lines. Tumor emboli culture: IBC cells are cultured in a polyethylene glycol (PEG)- or hyaluronic acid-containing medium in ultra-low attachment plates on a shaker plate, which mimics the viscosity and shear forces of lymphatic fluid. Hydrogel formulation: Acidified rat tail type I collagen (Fisher Scientific) will be neutralized with dilute sodium hydroxide at 4° C. The mixture will be deposited on top of the membranes containing confluent LEC monolayers to form a thin (<1 mm) hydrogel film. Viability assay: Samples of recirculating culture medium will be processed with trypan blue and hemacytometer analysis to obtain measurements of cell migration through the membrane and percent viability. Histological assessment: Transwell inserts will be removed from the systems, media removed, and flash frozen in liquid nitrogen. While frozen, the cell-collagen gel block will be removed from the transwell insert and processed for histologic cryosectioning. Sections will be obtained in the longitudinal (height-wise) plane. Sections will be air-dried at −80° C. overnight and fixed in chilled acetone for 10 min. Standard hematoxylin and eosin stains will be utilized. Immunohistochemistry will proceed as described in Example 2.

Experiment 1: Optimization of fluid flow. Initial testing of the system will involve optimization of flow rates to achieve a steady-state fluid level in the culture chamber. The flow rate will be high enough to support adequate mass transport to the tissue construct, though low enough to minimize shear stress on the monolayer. Lymph flow rates in the human thoracic duct are on the order of 1 mL/min, which will be used a preliminary outflow rate. However, because fluid transport within hydrogels is almost entirely limited to diffusion[24], this rate may be reduced. This experiment will be done in the absence of cells, though the hydrogel will be cast within the Transwell to provide flow resistance. The system will be tested for leakage, maintenance of steady state, required pump flow rates, and maximum flow rate across the hydrogel.

Experiment 2: Dynamic fluid transport through LEC monolayer. The first biological experiment will utilize human dermal LECs purchased from PromoCell. LECs will be expanded in culture and plated on the cell-permeable membrane in a standard well plate. After development of a confluent monolayer, the membrane will be transferred to the dynamic fluid chamber system. A collagen hydrogel will be deposited on the monolayer, then flow will be initiated. Viability measurement, cryosectioning, and H&E staining will be performed as described. Our expected results are that viability of the LEC monolayer will be maintained, with minimal migration through the membrane during the 24-hour time frame. An alternative strategy for this experiment is to culture the LEC monolayer on the bottom side of the membrane, as described by others. While this may serve to polarize the LEC monolayer, it is seen as disadvantageous because there is no direct contact with the hydrogel, and thus LEC-matrix interactions are removed from the model.

Experiment 3: Dynamic fluid transport through tumor emboli suspension, collagen hydrogel, and LEC monolayer. The third experiment will add a suspension of IBC tumor emboli above the hydrogel, thus representing the complete model system of LVI. LECs will plated, grown to confluency, and the hydrogel deposited. Tumor emboli will be formulated as described and transferred in culture medium to the space overlying the hydrogel. Viability measurement, cryosectioning, and H&E staining will be performed as described. Expected results are maintenance of viability of the LEC monolayer as well as invasion of the IBC cells into the hydrogel, through the LEC layer, and into the underlying fluid channel. As an alternative strategy, a basement membrane hydrogel (e.g. Matrigel™) will be used instead of type I collagen if significant invasion is not observed. Although breast cancer is known to proliferate throughout collagen gels, a basement membrane extract (e.g. Matrigel™) may provide a more robust substrate for invasion17. However, the use of a tumor membrane hydrogel does not fairly simulate the lymphovascular interstitium, which is (initially) comprised of benign, native cells.

Expected Results: We expect to produce histologic sections demonstrating IBC tumor emboli adhesion and invasion into the hydrogel, as well as interposition and invasion through the LEC monolayer.

Figure 1B:
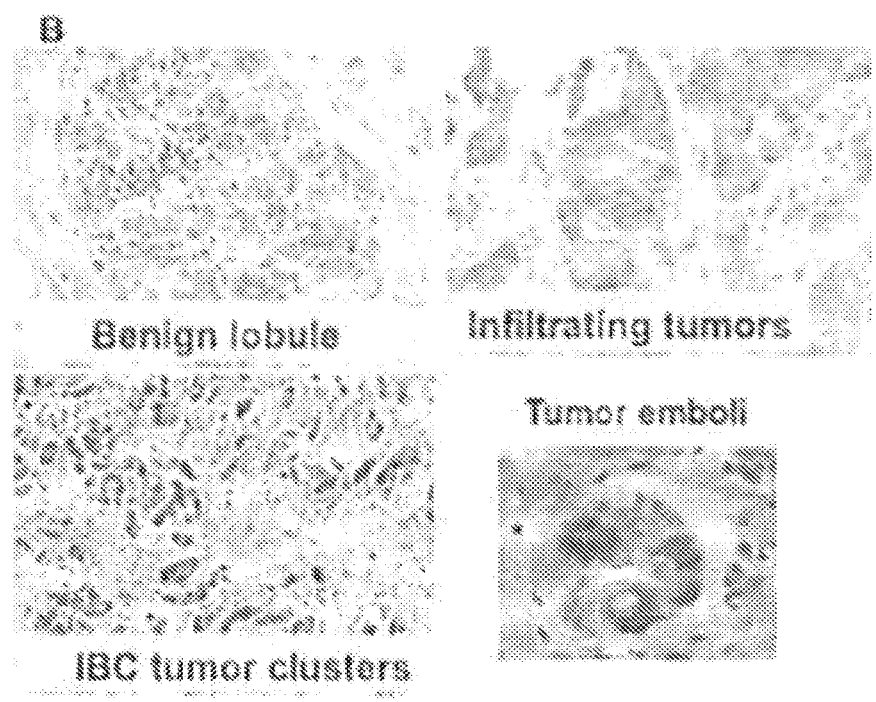
Figure 1C:
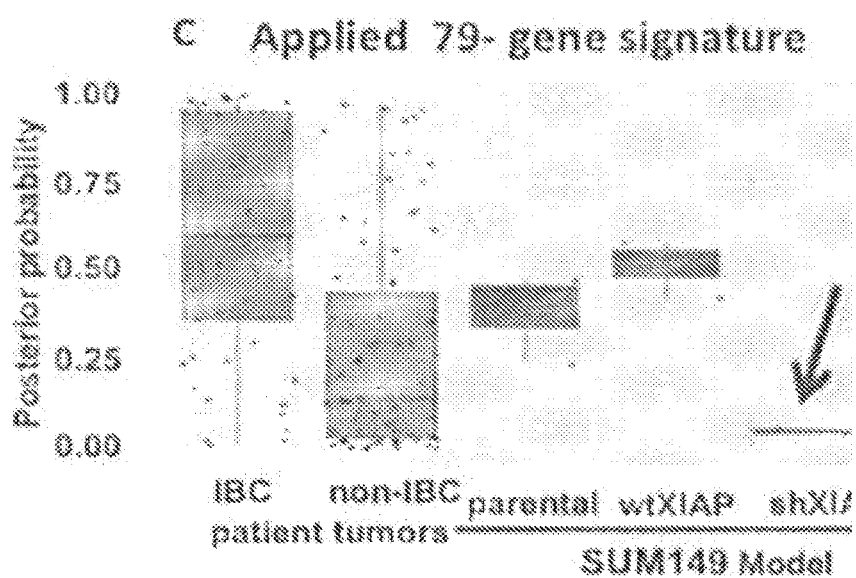

Example 2: Testing the Hypothesis that XIAP Promotes Invasion of IBC Tumor Emboli In Vitro Rationale: As previously discussed, XIAP is a key regulator of NFκB hyperactivation, which has been implicated in IBC progression. Our preliminary data (FIG. 1) demonstrate that mice overexpressing XIAP exhibit enhanced tumor growth as well as an increased rate of metastasis. Conversely, knockdown of XIAP in mice completely incapacitated tumor growth, which was reversed by reconstitution with the XIAP protein. In the XIAP knockdown mice, gene expression analysis revealed a total disappearance of the 79-gene signature, highlighting the critical role of this single gene in the immunosuppressive phenotype [REF]. The next step is to determine the contribution of XIAP to IBC invasion, which will be investigated with the proposed model. Specifically, we will quantify the number of invaded cells with the new model, as well as assess gene expression of the ECM-degrading enzyme MMP-9. Example 2 will utilize tumor cells harvested from mice with knockdown (shXIAP) or overexpressed (wtXIAP) XIAP, which have been well-characterized in our lab.

Methods: Invasion of tumor cells will be assessed with the new model as described in Example 1. shXIAP and wtXIAP cell lines will be directly compared with the new model. Cell invasion will be quantified and histologically sectioned as described in Example 1. Hydrogel sections will be stained for MMP-9. Expected results are that wtXIAP cells will exhibit a greater number of invaded cells, with higher expression of MMP-9, than shXIAP cells. Histological sections will be processed through immunofluorescence staining for the MMP-9 enzyme in the histology core. Specimens will be imaged with fluorescent microscopy.

Expected Results: This experiment is expected to confirm that XIAP enhances invasion in vitro through expression of MMP-9. We anticipate that wtXIAP cells demonstrate consistent elaboration of MMP-9 throughout the hydrogel in comparison to shXIAP cells. We also expect a higher number of invaded cells collected in the circulating medium, indicating a greater number of invaded cells. These data will support the role of XIAP in LVI as a critically important event in cancer metastasis.

Example 3: The Invasion Model Offers a Novel Clinical Assay for IBC Patients

Rationale: After initial testing of the model with established IBC cell lines, we will proceed with testing of primary human cells. As discussed previously, TNBC patients exhibit poorer clinical outcomes compared with non-TNBC, which is largely due to an incomplete understanding of the underlying biology. By studying LVI of a given patient's tumor cells in a system containing their own LECs, we may be able to gain crucial information about the invasiveness of the cancer and prognosis. The experiment proposed is a simple proof-of-concept of this clinical assay, and is not intended to assess information about the donor patients' cancers.

Methods: All human research will proceed under approval from the IRB (submission pending). A small number of consenting patients who have TNBC and are undergoing mastectomy for IBC will be included in the study. Tumor cells from IBC mastectomy specimens will be isolated as described by others. Briefly, partial mastectomy specimens will be received from the surgical team, minced into fragments, and digested overnight with collagenase and hyaluronidase. Cells will be pelleted and supernatant containing fat removed, which produces a heterogeneous population of tumor and stromal cells. For invasion testing, further purification will not be attempted. Dermal lymphatic endothelial cells will be isolated from breast skin as described by others. Briefly, skin containing dermis will be surgically separated from underlying subcutaneous tissue and incubated with dispase 50 u/mL for 30 min at □C. Cells will be centrifuged and resuspended in EC growth medium MV (PromoCell) and seeded onto fibronectin-coated dishes. After expansion in culture, plate-adherent EC cells will be sorted with flow cytometry into a podoplanin+CD34+LEC subpopulation. Confirmatory analysis for LEC-specific gene expression will be done by immunoblotting for podoplanin, LYVE-1, and VEGF-CR. Use of the invasion model will be performed as described in Example 1. Cell invasion will be quantified and histologically sectioned as described in Example 1. Hydrogel sections will be stained for MMP-9.

Any patents or publications mentioned in this specification are indicative of the levels of those skilled in the art to which the invention pertains. These patents and publications are herein incorporated by reference to the same extent as if each individual publication was specifically and individually indicated to be incorporated by reference. In case of conflict, the present specification, including definitions, will control.

One skilled in the art will readily appreciate that the present invention is well adapted to carry out the objects and obtain the ends and advantages mentioned, as well as those inherent therein. The present disclosure described herein are presently representative of preferred aspects, are exemplary, and are not intended as limitations on the scope of the invention. Changes therein and other uses will occur to those skilled in the art which are encompassed within the spirit of the invention as defined by the scope of the claims.

Although the invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. An in vitro 3-D lymphovascular system comprising:
   (a) a fluid chamber comprising medium in liquid communication with a transwell and a fluid pump,
   (b) the transwell comprising a permeable membrane separating a basolateral surface and an apical compartment of the transwell, wherein the apical compartment of the transwell comprises:
      (i) lymphatic endothelial cells (LECs) seeded on the apical surface of the permeable membrane;
      (ii) a layer of hydrogel above the seeded LECs layer, and
      (iii) medium comprising tumor cells; and
   (c) a fluid pump capable of creating steady-state flow rate of medium throughout the fluid chamber and transwell of the system.

2. The lymphovascular system of claim 1, wherein the tumor cells are breast cancer cells.

3. The lymphovascular system of claim 1, wherein the tumor emboli from inflammatory breast cancer.

4. The lymphovascular system of claim 1, wherein the hydrogel of (ii) is collagen hydrogel.

5. The lymphovascular system of claim 1, wherein the lymphatic endothelial cells and the tumor cells are from a patient having cancer.

6. The lymphovascular system of claim 5, wherein the patient has breast cancer.

7. The lymphovascular system of claim 6, wherein the patient has inflammatory breast cancer.

8. The lymphovascular system of claim 6, wherein the patient has triple negative breast cancer.

9. The lymphovascular system of claim 1, wherein the lymphatic endothelial cells provide a monolayer on the permeable membrane.

10. The lymphovascular system of claim 1, wherein the permeable membrane has a pore diameter of about 5 μm to about 8 μm.

11. The lymphovascular system of claim 1, wherein the layer of hydrogel is about 0.5 mm to about 2 mm thick.

12. A method of testing the efficacy of an anti-cancer therapy, the method comprising contacting the 3-D lymphovascular system of claim 1 with the anti-cancer therapy; and measuring the efficacy of the therapy.

13. The method of claim 12, wherein the efficacy of the therapy is measured by the ability of the anti-cancer drug to kill tumor cells in the 3-D lymphovascular system.

14. The method of claim 12, wherein the anti-cancer therapy is an anti-cancer drug.

15. The method of claim 12, wherein the anti-cancer therapy is a combination of two or more anti-cancer drugs.

16. A method of screening for a patient-specific anticancer therapy, the method comprising: contacting a plurality of 3-D lymphovascular systems of claim 5 each with a different anticancer therapy, and assessing the efficacy of each anticancer therapy against the patient specific tumor cells in the system.

17. The method of claim 16, wherein the cancer is breast cancer.

\* \* \* \* \*